United States Patent [19]

Ferrari et al.

[11] 4,045,555

[45] Aug. 30, 1977

[54] METHOD FOR THE PHOTOSTABILIZATION OF POLYHYDROXYLATED STEROLS AND STABILIZED BIOLOGICAL INSECTICIDAL PRODUCT OBTAINED THEREBY

[75] Inventors: Giorgio Ferrari; Luigi Canonica, both of Milan; Bruno Danieli, Cesano Maderno (Milan), all of Italy

[73] Assignee: Dauten S.A., Switzerland

[21] Appl. No.: 292,295

[22] Filed: Sept. 26, 1972

[30] Foreign Application Priority Data

Sept. 29, 1971 Italy .................................. 29276/71

[51] Int. Cl.² .............................................. A01N 9/24
[52] U.S. Cl. ............................. 424/174; 424/DIG. 12
[58] Field of Search ........................ 424/174, DIG. 12

[56] References Cited

U.S. PATENT DOCUMENTS 3,189,615  6/1965  Heller et al. ........................ 424/174

3,453,362  7/1969  Cruickshank .......................... 424/84

FOREIGN PATENT DOCUMENTS 1,159,137  7/1967  United Kingdom

OTHER PUBLICATIONS

Chemical Abstracts, vol. 64 (1966), p. 14642b.

*Primary Examiner*—V. D. Turner
*Attorney, Agent, or Firm*—Shlesinger, Fitzsimmons & Shlesinger

[57] ABSTRACT

Insect metamorphosis hormones of the polyhydroxylated sterol type are light sensitive and tend to lose their activity under the action of light, especially UV radiations. An insect controlling formulation is suggested herein, which contains, in addition to the insect metamorphosis hormones, photostabilizing substances such as benzotriazoles, substituted phenylglioxylic acids and salts thereof.

3 Claims, No Drawings

METHOD FOR THE PHOTOSTABILIZATION OF POLYHYDROXYLATED STEROLS AND STABILIZED BIOLOGICAL INSECTICIDAL PRODUCT OBTAINED THEREBY

This invention relates to the photostabilization of hormones of the metamorphosis of insects, which can be used as biological insecticides.

During progress of prior studies, the Applicants have indicated new preparations having a biological insecticidal activity, which contained insect metamorphosis hormones, more particularly ecdisone, crustecdisone, makisterone A and muristerone, as more detailedly disclosed in the U.S. Patent application Ser. No. 217,842 filed on Jan. 14, 1972 issued Aug. 6, 1974 as U.S. Pat. No. 3,828,082, in the name of the same Applicants, which is referred to herein for greater details.

It has been ascertained, however, that these hormones belonging to the class of polyhydroxylated sterols and more exactly to that of ecdisterols, whose molecule contains a conjugated ketone grouping, are sensitive to the light.

As a matter of fact, the exposure to sunlight causes within a short time destructive deteriviation of these substances, both in the solid state and in solution. This fact restricts the possibility of using the above enumerated hormones of insect metamorphosis in formulations intended over a prolonged period of time to control the population of noxious insects, since the molecular structure of these hormones cannot be kept unaltered for an adequately long time.

It has now been found, and this is the subject matter of the present invention, that the problems, as briefly outlined above, are radically solved, while obtaining an efficient protection against the degradation of these sterols as caused by light, if they are associated with adequate photoprotective substances which are capable of neutralizing beforehand the destructive effects of ultraviolet radiations.

The stabilization process according to the present invention is characterized thus in that ecdisterols, which are useful as biological-action insecticides, are admixed with stabilizing amounts of absorbent and photoprotective substances. More particularly, the objects of the present invention are attained when the compounds which absorb the ultraviolet radiations are selected from among those which are conventionally used for protecting plastics materials, such as o-hydroxybenzophenones, benzotriazoles and substituted phenylglioxylic acids and their salts. Most advantageous results are obtained when the stabilizer is selected from the last two classes of compounds.

The biological insecticidal product according to the present invention, in turn, is characterized in that it contains, as the active principle, one or more hormones of insect metamorphosis and, as the stabilizer, a photoprotective substance which is capable of neutralizing the destructive effects of ultraviolet radiations.

The concentrations, which are recommendable for these substances having a protective action against ultraviolet rays in order that a stabilizing effect may be obtained and thus the protection of the insect metamorphosis hormones, vary according to the characteristics of the formulation and are comprised between 0.005 and 5 grams per 100 parts by weight of the final formulate. In general, concentrations ranging from the lower limiting value indicated above to a weight equal to that of the hormones, which are present in the formulation, are sufficient.

The stabilizing effects of the photoprotective and UV-ray absorbing substances indicated above are displayed for dosages such as suggested in the foregoing and for a period of time which is sufficient to ensure the biological action of the metamorphosis hormones.

Another aspect which is very important from the point of view of the application as biological insecticides of the insect metamorphosis hormones lies in that, by varying the amount of photostabilizing substances present in the formulation, it is possible to govern as desired the useful life or duration of the stability period of the insecticidal product, before the latter undergoes the photochemical action and the insecticidal action may disappear.

The metamorphosis hormones, which among others are sensitive to stabilization, are for example: ecdisone, crustecdisone, (ecdisterone or ecdisone beta), makisterone A, muristerone. In addition, a total extract containing ecdisterols and the substances indicated above is appropriately stabilized for use. Such an extract is obtained according to the teachings of the aforementioned patent application.

For the practical preparation of stabilized compositions of insect metamorphosis hormones, the photostabilizers should be intimately admixed with the active principle (s) and the other constituents of the formulation if said powdered preparations are intended. In the case of liquid formulates, either in solution or in suspension, the stabilizer, as dissolved in appropriate solvent in the form of a master solution, is added to the solution, or suspension as the case may be, of the hormone (s) of the metamorphosis and the other components.

As solvents which are adapted to the preparation of the master solutions of photostabilizers belonging to the class of benzotriazoles, one can use, for example: acetone, ethyl acetate, butyl acetate, benzene, toluene, ethanol, methanol, ligroin.

In the case of derivatives of phenylglioxylic acid and its salts, one can employ, instead, for the preparation of the master solutions, glycerol, 1,2-propanediol, nor. propanol, polyethylene glycols and vegetable oils. Lastly, aqueous master solutions can be prepared for phenylglioxylic acid salts.

The stabilized solutions of metamorphosis hormones can also be prepared by concurrently dissolving in one of the above indicated solvents, or in admixtures of the above indicated solvents, the photostabilizer and the hormone (s); subsequently this solution can be dispersed in the excipient or the solid components of the formulation and then the solvent(s) are evaporated by mere exposure to air or by keeping the mass under vacuum. The dried residue can then be finely ground and the powder used as such, or the residue can be taken up, in turn, with appropriate solvents in order to obtain a concentrate. The stabilized preparations of insect metamorphosis hormones as obtained after the criteria indicated above and as more detailedly disclosed in the following examples can be used either directly as insecticides or they can be introduced in more complex formulations.

The ensuing examples are given by way of suggestion only and do not limit the scope of the present invention

EXAMPLE 1

10 grams of crustecdisone (ecdisterone, beta ecdisone) are combined with 0.5 grams of an alkylated 2-(2- hydroxyphenyl)-2H-benzotriazole (such as Tinuvin 327). The two products should have been previously ground to a mesh size of 60 mesh/centimeter. The powder is shaken in a powder mixture until obtaining a homogenous admixture of the two substances. The thusly obtained composition is a stabilized crustecdisone composition.

EXAMPLE 2

The procedure is similar to that of Example 1, by employing instead of crustecdisone the same amount of an extract which contains crustecdisone, makisterone A, ecdisone, muristerone and other polyhydroxylated sterols.

EXAMPLE 3

In 250 mls acetone there are dissolved 1 gram of ecdisone and 100 milligrams of an alkylated 2-(2-hydroxyphenyl)-2H-benzotriazole (such as Tinuvin 328). The solution in acetone is spread, in a mixer, over one kilogram of airclassified talc powder. Acetone is removed from the mass by keeping it in a desiccator under vacuum heated at 40° C until completely evaporating of the solvent.

A stabilized crustecdisone preparation is thus obtained.

EXAMPLE 4

The procedure is akin to that of Example 3, ecdisone being employed instead of ecdisterone.

EXAMPLE 5

0.5 grams of crustecdisone are weighed and dissolved at 50° C in 200 mls of 1,2-propanediol. There are weighed 25 milligrams of an alkyl substituted 2-(2-hydroxyphenyl)-2H-benzotriazole (such as Tinuvin 327) and are dissolved in 175 mls of 1,2-propanediol. This second solution is combined with the first one and then water is added to make up to 500 mls. The thusly obtained solution is a stabilized crustecdisone solution.

EXAMPLE 6

The procedure is similar to that of Example 5 by using makisterone A in lieu of crustecdisone.

EXAMPLE 7

2 grams of ecdisterone are weighed. 60 grams of polyvinyl pirrolidone are weighed separately. The two products are dissolved in 100 mls and 600 mls of ethyl alcohol, respectively. A solution of 10% by vol. of the sodium salt of a substituted phenylglioxylic acid in water is prepared (such as Eusolex 161). The two alcoholic solutions are combined and evaporated to dryness in a rotary evaporator at the maximum temperature of 50° C up to complete dryness. The glassy residue is supplemented with 20 mls of the master solution of Eusolex 161 and then it is taken up with water to make up one liter.

A stabilized ecdisterone aqueous solution is thus obtained.

EXAMPLE 8

The procedure is similar to that of Example 7 using in lieu of ecdisterone, 2 grams of an extract made of crustecdisone, makisterone A, ecdisone, muristerone and other polyhydroxylated sterols.

EXAMPLES 9 and 10

The protective activity of the photostabilizers according to the invention against the degradation originated by light, or, under more unfavourable conditions, by UV radiations on the above mentioned insect metamorphosis hormones has been tested experimentally, the results being those tabulated in the following Tables.

The tests have been carried out on solutions containing, dissolved in methanol, determined amounts of crustecdisone (Ex. 9) and muristerone (Ex. 10), in the presence of gradually increasing amounts of different photoprotective, UV-absorbing compounds, which, in both the examples, were represented by: Tinuvin 327 and 328 (for the benzotriazole class) Eusolex (for the class of substituted phenylene glioxylic acids).

The last test reported in the Tables is the one relative to the hormone as such, without photostabilizer, kept in the dark.

Each test is the average of five readings. The quantitative determination of the hormone is carried out by chromatographic separation on a thin layer using as the eluent system a mixture of methylene chloride:methanol:water in the ratios 79:15:1 on prepared Merck Kieselgel F 254 art. 5715 plates. The spots are then quantitatively evaluated with a Vitatron densometer. All the tests are referred to measurements taken after exposure to the light of a Philips HPK 125 lamp during a period of one hour and a half.

TABLE 1

| | CRUSTECDISONE | | | | | |
|---|---|---|---|---|---|---|
| | EUSOLEX | | TINUVIN 327 | | TINUVIN 328 | |
| Test | Weight ratio Hormone/ stabilizer | % surviving hormone | Weight ratio Hormone/ stabilizer | % surviving hormone | Weight ratio Hormone/ stabilizer | % surviving hormone |
| 1 | 14/1 | 0 | 9.4/1 | 27 | 9.7/1 | 29 |
| 2 | 7/1 | 27 | 4.7/1 | 52 | 4.85/1 | 84 |
| 3 | 4.67/1 | 44 | 3.12/1 | 66 | 3.23/1 | 90 |
| 4 | 3.5/1 | 94.5 | 2.35/1 | 92 | 2.42/1 | 95 |
| 5 (light) | — | 0 | — | 0 | — | 0 |
| 6 (dark) | — | 100 | — | 100 | — | 100 |

TABLE 2

| | MURISTERONE | | | | | |
|---|---|---|---|---|---|---|
| | EUSOLEX | | TINUVIN 327 | | TINUVIN 328 | |
| Test | Weight ratio Hormone/ stabilizer | % surviving hormone | Weight ratio Hormone/ stabilizer | % surviving hormone | Weight ratio Hormone/ stabilizer | % surviving hormone |
| 1 | 10.1/1 | 0 | 9.45/1 | 42.5 | 9.85/1 | 66.5 |
| 2 | 5.05/1 | 26.0 | 4.73/1 | 65.5 | 4.93/1 | 80 |

TABLE 2-continued

| | EUSOLEX | | MURISTERONE TINUVIN 327 | | TINUVIN 328 | |
|---|---|---|---|---|---|---|
| Test | Weight ratio Hormone/ stabilizer | % surviving hormone | Weight ratio Hormone/ stabilizer | % surviving hormone | Weight ratio Hormone/ stabilizer | % surviving hormone |
| 3 | 3.37/1 | 43 | 3.15/1 | 78.5 | 3.29/1 | 100 |
| 4 | 2.66/1 | 93 | 2.37/1 | 96 | 2.47/1 | 100 |
| 5 (light) | — | 0 | — | 0 | — | 0 |
| 6 (dark) | — | 100 | — | 100 | — | 100 |

The time of 1.5 hours has been selected on the basis of the fact that this is the time required for the total destruction of the hormone which is present in the non-protected solution exposed to the lamp light.

The data reported in the Tables show that it is possible to govern the duration of the photostabilization in relation with the quantity of photostabilizer used, that the absence of photostabilizer rapidly leads to the disappearance of the hormone which is present in the solution, and that all the adopted photostabilizers are active as protective agents.

What we claim is:

1. A biological insecticide formulate comprising
   an insect metamorphosis hormone which deteriorates in light, and
   a stabilizing photoprotective compound mixed with said hormone in an amount ranging between a lower limit of 0.005 grams per 100 parts by weight of the final formulate, and an upper limit in which said compound equals the weight of said hormone, and selected from the group consisting of benzotriazoles, and substituted phenylglioxylic acids and their salts.

2. A method for producing a biological insecticide, which comprises
   mixing with insect metamorphosis hormones of the polyhydroxylated sterol type, whose molecule contains a conjugated ketone grouping, in a formulation an amount between 0.005 and 5 grams per 100 parts by weight of the final formulate a substance which is capable of neutralizing the destructive effects on said hormones of ultraviolet radiation and which is selected from the group consiting of 0-hydroxybenzophenones, benzotriazoles, substituted phenylglioxylic acids and salts thereof, to extend the useful life of said formulation.

3. A method according to claim 2 wherein said stabilizing substance is added in an amount by weight which is equal to the weight of the insect metamorphosis hormones present in said formulation.

* * * * *